(12) United States Patent
McCormick (10) Patent No.: US 9,064,357 B1
(45) Date of Patent: Jun. 23, 2015

(54) VEHICLE DYNAMICS CONTROL USING INTEGRATED VEHICLE STRUCTURAL HEALTH MANAGEMENT SYSTEM

(75) Inventor: Patrick Joseph McCormick, Mercer Island, WA (US)

(73) Assignee: THE BOEING COMPANY, Chicago, IL (US)

( * ) Notice: Subject to any disclaimer, the term of this patent is extended or adjusted under 35 U.S.C. 154(b) by 388 days.

(21) Appl. No.: 13/469,030

(22) Filed: May 10, 2012

(51) Int. Cl.
  *G05D 15/00* (2006.01)
  *G07C 5/08* (2006.01)
  *G01M 5/00* (2006.01)
  *G05D 15/01* (2006.01)
  *G01N 27/20* (2006.01)
  *G01L 1/24* (2006.01)

(52) U.S. Cl.
  CPC ........... *G07C 5/0816* (2013.01); *G01M 5/0016* (2013.01); *G05D 15/01* (2013.01); *B64C 2700/6264* (2013.01); *G01N 27/20* (2013.01); *G01L 1/246* (2013.01)

(58) Field of Classification Search
  CPC ........ B64C 7/00; B64C 27/00; B64C 27/001; B64C 27/006; B64C 27/007; B64C 2700/6264; B64C 2700/6266; B64D 2045/00; B64D 2045/008; B64D 2045/0085; B64D 2700/62043; B82Y 30/00; G01D 5/268; G01D 5/00; G01D 5/24; G01D 5/241; G01D 5/242; G01D 5/243; G01D 5/245; G01D 5/246; G01M 3/00; G01M 3/36; G01M 3/40; G01M 5/00; G01M 5/0016; G01M 5/0025; G01M 5/0033; G01M 5/0041; G01M 5/005; G01M 5/0058; G01M 5/0066; G01M 5/0075; G01M 5/0083; G01M 5/0091; G01M 9/06; G01M 99/00; G01M 99/002; G01M 99/004; G01M 9/005; G01M 9/008; G01N 2033/0083; G01N 27/20; G05D 15/00; G05D 15/01
  USPC ...................................... 701/3, 29.1
  See application file for complete search history.

(56) References Cited

U.S. PATENT DOCUMENTS

| 5,775,715 | A | 7/1998 | Vandergrift | |
|---|---|---|---|---|
| 7,786,736 | B2 | 8/2010 | Thostenson et al. | |
| 2007/0118301 | A1* | 5/2007 | Andarawis et al. | 702/33 |
| 2009/0153144 | A1* | 6/2009 | Hansen | 324/511 |
| 2010/0017049 | A1 | 1/2010 | Swearingen et al. | |
| 2011/0245999 | A1* | 10/2011 | Kordonowy | 701/3 |

OTHER PUBLICATIONS

"The C-5A Active Load Alleviation System", AIAA Paper 75-991, by T.E. Disney (Lockheed-Georgia Co.), Aug. 4-7, 1975.
"Investigation of Structural Properties of Carbon-Epoxy Composites Using Embedded Fiber-Optic Bragg Gratings", by Osei, Albert, Oaskwood College Math and Physics Dept. in coordination with NASA Faculty Fellowship Program, 2002.

* cited by examiner

*Primary Examiner* — Jerrah Edwards
(74) *Attorney, Agent, or Firm* — Ameh IP; Elahe Toosi; Lowell Campbell (57) ABSTRACT

A system and methods for alleviating an anomaly in a structure are presented. At least one anomaly detector structural member is embedded in the structure. A measurement signal is sent to the anomaly detector structural member and a feedback signal is received from the anomaly detector structural member in response to the measurement signal. A difference between the measurement signal and the feedback signal is calculated to determine a change in the structure, and at least one non-optimal event is identified in real-time if the change exceeds an event threshold.

20 Claims, 6 Drawing Sheets

VEHICLE DYNAMICS CONTROL USING INTEGRATED VEHICLE STRUCTURAL HEALTH MANAGEMENT SYSTEM

FIELD

Embodiments of the present disclosure relate generally to methods and systems for active control. More particularly, embodiments of the present disclosure relate to real-time active control of a structure.

BACKGROUND

In some conditions, excessive design conservatism in structures such as a vehicle or an airplane structure due to performance, regulatory, theoretical, or other constraints adds weight to the vehicle and reduces performance such as, for example, increasing fuel burn. Current solutions generally require a deep understanding of theory and physics of systems and also generally require backing up theory with more testing, and decreasing structural design conservatism. Decreasing structural design conservatism may avoid reducing performance requirements margins of the vehicle so designed.

SUMMARY

A system and methods for alleviating an anomaly in a structure are presented. At least one anomaly detector structural member is embedded in the structure. A measurement signal is sent to the anomaly detector structural member and a feedback signal is received from the anomaly detector structural member in response to the measurement signal. A difference between the measurement signal and the feedback signal is calculated to determine a change in the structure, and at least one non-optimal event is identified in real-time if the change exceeds an event threshold.

In this manner, a weight of the structure such as a vehicle is reduced where a design of structural parts to meet structural design goals for survivability between maintenance intervals, performance requirements, etc. are conservative. Using an active feedback from an integrated vehicle structural health management (IVHM) system allows controlling the vehicle closer to a limit of a structural design and getting a same performance while still meeting lifetime survivability goals.

In an embodiment, a method for alleviating an anomaly in a structure embeds at least one anomaly detector structural member in the structure. The method then sends a measurement signal to the anomaly detector structural member and receives a feedback signal from the anomaly detector structural member in response to the measurement signal. The method then calculates a difference between the measurement signal and the feedback signal to determine a change in the structure, and identifies at least one non-optimal event in real-time if the change exceeds an event threshold.

In another embodiment, a system for alleviating an anomaly in structure in real-time, comprises a structure, at least one anomaly detector structural member embedded in the structure, a measurement signal generator, a sensor, a structural health metrics calculator, an event identifier module, and a control initiation module. The measurement signal generator sends a measurement signal to the anomaly detector structural member. The sensor receives a feedback signal from the anomaly detector structural member in response to the measurement signal. The structural health metrics calculator calculates a difference between the measurement signal and the feedback signal to determine a change in the structure. The event identifier module identifies at least one non-optimal event in real-time if the change exceeds an event threshold. And the control initiation module activates a control mechanism in response to an active control command in real-time to compensate for the non-optimal event.

In a further embodiment, a flight control method for actively compensating for a non-optimal event in an aircraft structure in-flight receives a feedback signal from at least one anomaly detector structural member embedded in the aircraft structure in response to a measurement signal. The method then calculates a difference between the measurement signal and the feedback signal to determine a change in the aircraft structure. The method further identifies at least one non-optimal event in real-time if the change exceeds an event threshold in-flight. The method further compensates for the non-optimal event by activating at least one flight control surface in real-time in response to a control command.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF DRAWINGS

A more complete understanding of embodiments of the present disclosure may be derived by referring to the detailed description and claims when considered in conjunction with the following figures, wherein like reference numbers refer to similar elements throughout the figures. The figures are provided to facilitate understanding of the disclosure without limiting the breadth, scope, scale, or applicability of the disclosure. The drawings are not necessarily made to scale.

DETAILED DESCRIPTION

The following detailed description is exemplary in nature and is not intended to limit the disclosure or the application and uses of the embodiments of the disclosure. Descriptions of specific devices, techniques, and applications are provided only as examples. Modifications to the examples described herein will be readily apparent to those of ordinary skill in the art, and the general principles defined herein may be applied to other examples and applications without departing from the spirit and scope of the disclosure. The present disclosure should be accorded scope consistent with the claims, and not limited to the examples described and shown herein.

Embodiments of the disclosure may be described herein in terms of functional and/or logical block components and various processing steps. It should be appreciated that such block components may be realized by any number of hardware, software, and/or firmware components configured to perform the specified functions. For the sake of brevity, conventional techniques and components related to control laws, control systems, elasticity measurement techniques, measurement sensors, data transmission, signaling, network control, and other functional aspects of the systems (and individual operating components of the systems) may not be described in detail herein. In addition, those skilled in the art will appreciate that embodiments of the present disclosure may be practiced in conjunction with a variety of hardware and software, and that the embodiments described herein are merely example embodiments of the disclosure.

Embodiments of the disclosure are described herein in the context of a practical non-limiting application, namely, active control of an aircraft structure. Embodiments of the disclosure, however, are not limited to such aircraft structure control, and the techniques described herein may also be utilized in other applications. For example but without limitation, embodiments may be applicable to manned and unmanned ground, air, space, water and underwater vehicles, buildings, windmills, or other structure.

As would be apparent to one of ordinary skill in the art after reading this description, the following are examples and embodiments of the disclosure and are not limited to operating in accordance with these examples. Other embodiments may be utilized and structural changes may be made without departing from the scope of the exemplary embodiments of the present disclosure.

Figure 1:
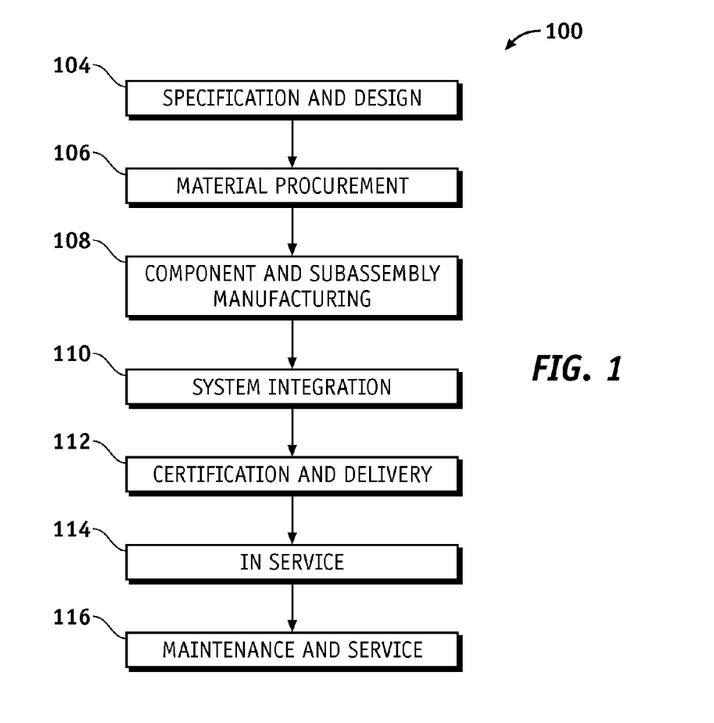
FIG. 1 is an illustration of a flow diagram of an exemplary aircraft production and service methodology.
Figure 2:
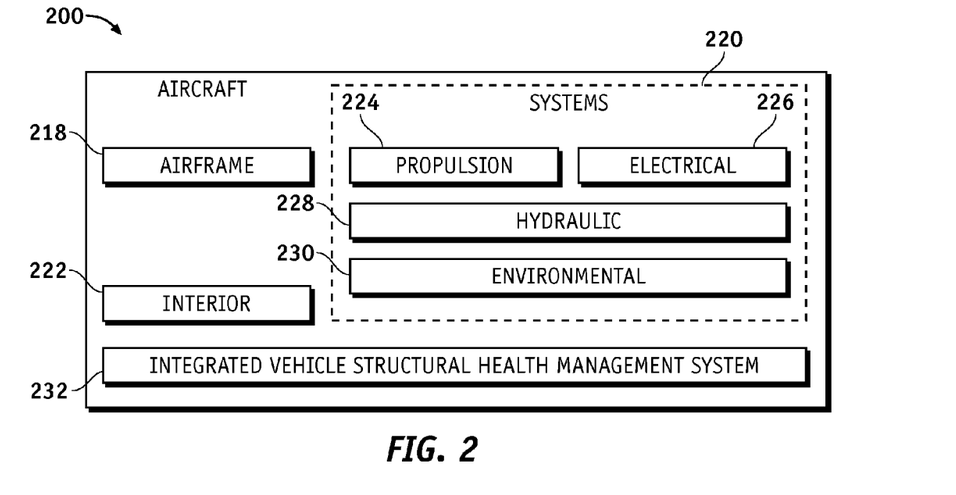
FIG. 2 is an illustration of an exemplary block diagram of an aircraft.

Referring more particularly to the drawings, embodiments of the disclosure may be described in the context of an aircraft manufacturing and service method 100 (method 100) as shown in FIG. 1 and an aircraft 200 as shown in FIG. 2. During pre-production, the exemplary method 100 may include specification and design 104 of the aircraft 200 and material procurement 106. During production, component and subassembly manufacturing 108 and system integration 110 of the aircraft 200 takes place. Thereafter, the aircraft 200 may go through certification and delivery 112 in order to be placed in service 114. While in service by a customer, the aircraft 200 is scheduled for routine maintenance and service 116 (which may also include modification, reconfiguration, refurbishment, and so on).

Each of the processes of method 100 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be without limitation an airline, leasing company, military entity, service organization, and the like.

As shown in FIG. 2, the aircraft 200 produced by the exemplary method 100 may include an airframe 218 with a plurality of systems 220 and an interior 222. Examples of high-level systems 220 include one or more of a propulsion system 224, an electrical system 226, a hydraulic system 228, an environmental system 230, and an integrated vehicle structural health management system 232. Any number of other systems may also be included. Although an aerospace example is shown, the embodiments of the disclosure may be applied to other industries.

Apparatus and methods embodied herein may be employed during any one or more of the stages of the production and service method 100. For example, components or subassemblies corresponding to production process 108 may be fabricated or manufactured in a manner similar to components or subassemblies produced while the aircraft 200 is in service. In addition, one or more apparatus embodiments, method embodiments, or a combination thereof may be utilized during the production stages 108 and 110, for example, by substantially expediting assembly of or reducing the cost of an aircraft 200. Similarly, one or more of apparatus embodiments, method embodiments, or a combination thereof may be utilized while the aircraft 200 is in service, for example and without limitation, to maintenance and service 116.

Embodiments of the disclosure use an active feedback from embedded IVHM systems to actively control the aircraft 200 in real-time or near-real-time for the purpose of alleviating the non-optimal events such as but without limitation, a stress, a vibration or flutter, a flexure, an excessive bending, a propulsion system anomaly, an excessive linear displacement, an excessive angular displacement, a structural fatigue, a control surface anomaly, a lift surface anomaly, or other non-optimal event. The embodiments also provide active control of the structure to lower fatigue stress detected (via a long-term measurement database), thereby prolonging structural life and reducing time between maintenance events.

Feedback from the IVHM systems embedded in a structure of a vehicle is measured by sensors and is fed back to a system such as a flight control electronics which controls dynamics of the vehicle. In this manner, effectively another feedback loop is created between an inherent physics of the vehicle and the dynamics control (control laws) with the structural members of the vehicle comprising the IVHM system. This feedback loop enables the control algorithm to control to a new set of variables including structural health metrics. Using an active feedback such as the feedback signal from the embedded IVHM allows controlling the vehicle such as the aircraft 200 closer to a limit of the structural design and provides a same performance while meeting lifetime survivability goals.

The term real-time refers to a signal that is continuously being sent and received, with little or no time delay. The term near-real-time refers to a real-time signal with substantially no significant time delay. The time delay may be a delay introduced by, for example but without limitation, automated data processing or network transmission, between occurrence of an event, and the like. In this document, the term real-time refers to both real-time and near-real-time.

Figure 3:
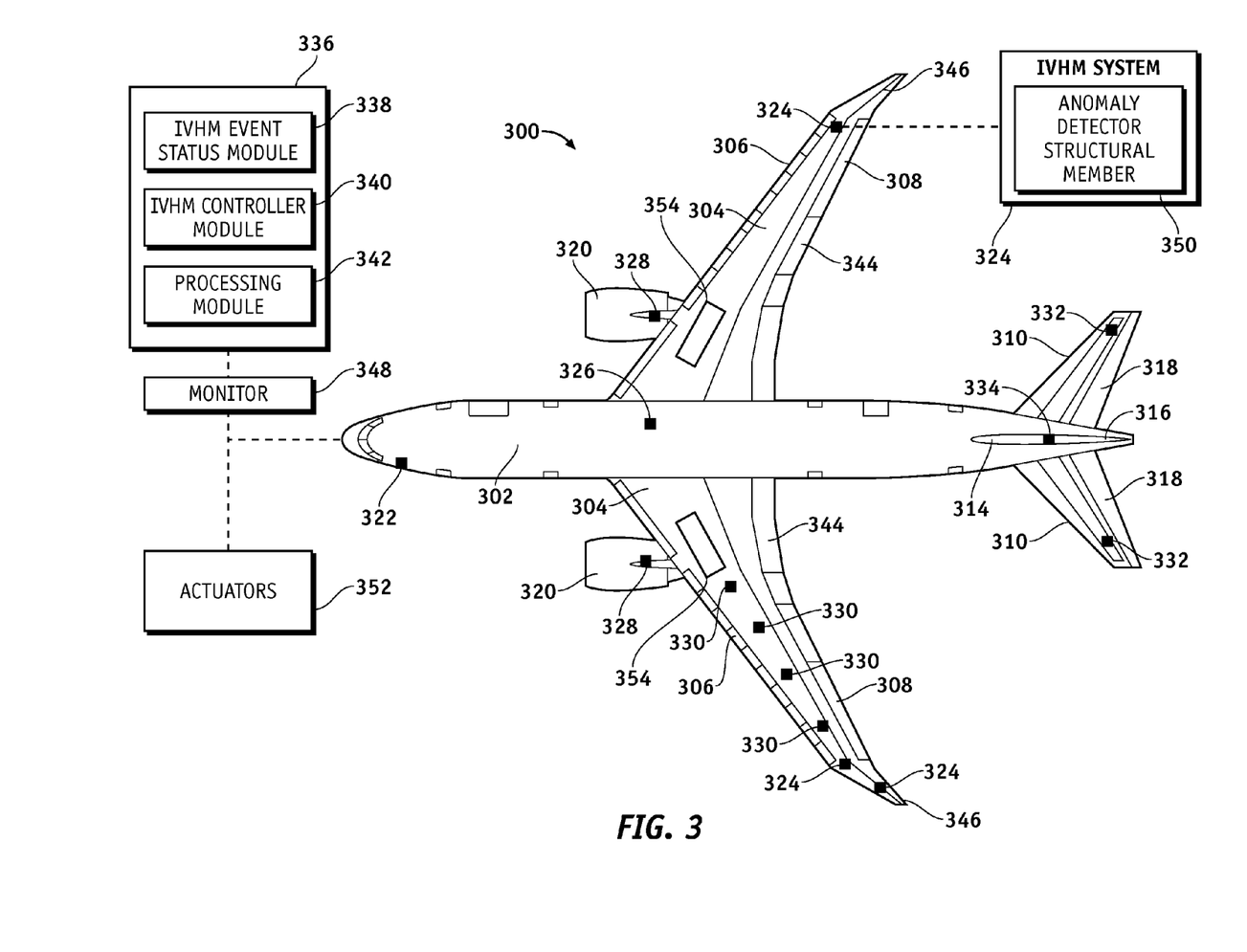
FIG. 3 is an illustration of an exemplary aircraft comprising a plurality of integrated vehicle structural health management (IVHM) systems each comprising at least one anomaly detector structural member according to an embodiment of the disclosure.

FIG. 3 is an illustration of an exemplary aircraft 300 comprising a plurality of integrated vehicle structural health management (IVHM) systems each comprising at least one anomaly detector structural member 350 according to an embodiment of the disclosure. The aircraft 300 may comprise a control system 336, control surfaces 306/308/314/316/318/344/354, lift surfaces 302/304/310, and IVHM systems 324/328/330/332/334 each comprising at least one anomaly detector structural member 350.

The control system 336 is operable to activate the control surfaces 306/308/314/316/318/344/354 and the lift surfaces 302/304/310 in real-time to compensate for a non-optimal event, if the non-optimal event occurs. The control system 336 may comprise an IVHM event status module 338, an IVHM controller module 340, and a processing module 342 as explained in more detail in the context of discussion of FIG. 7 below.

The control surfaces 306/308/314/316/318/344/354 may comprise, for example but without limitation, a landing gear door (not shown), a flight control surface such as a slat 306, an aileron 308, a tail 314, a rudder 316, an elevator 318, a flap 344, a spoiler 354, or other control surface.

The lift surfaces 302/304/310 may comprise, for example but without limitation, a fuselage 302, a wing 304, a canard (not shown), a horizontal stabilizer 310, or other lift surface.

The IVHM systems 324/328/330/332/334 are integrated in the structure of the aircraft 300 and may be coupled to the processing module 342. Some embodiments may comprise, for example but without limitation, any number of IVHM systems embedded throughout the aircraft 300, and the location of such IVHM systems 324/328/330/332/334 need not be restricted to the locations shown in FIG. 3. Each of the IVHM systems 324/328/330/332/334 comprise at least one anomaly detector structural member 350 embedded therein. Each of the IVHM systems 324/328/330/332/334 allows use of active feedback therefrom to control the aircraft 300 closer to a limit of a structural design with substantially a same performance while meeting lifetime survivability metrics.

In the embodiments shown in FIG. 3, the IVHM systems 328 are located in the engine 320 struts, the IVHM systems 330 are located in the wing 304, as these locations represent structural areas of interest for which conditions may be monitored. The IVHM systems 322 may be located at a nose location to measure body bending and stress at that extreme. One skilled in the art will recognize many embodiments with more (or less) IVMH systems and different locations are possible. The IVHM systems 324/328/330/332/334 are explained in more detail in the context of discussion of FIGS. 4 and 5 below.

The aircraft 300 may also comprise a monitor 348 operable to collect data from IVHM systems 324/328/330/332/334, located at various measurement points of interest on the aircraft 300 as explained in more detail below.

The monitor 348 within the aircraft 300 is installed in the aircraft 300 to provide in-flight wing/tail/fuselage twist and deflection/extension/displacement data to a flight control system (not shown). The monitor 348 shown in FIG. 3 generally may comprise, for example but without limitation, a reference IVHM system 326 coupled to the processing module 342. The monitor 348 also collects measurement data from the reference IVHM system 326, which is preferably located in the fuselage 302. The reference IVHM system 326 is treated as a fixed reference point that is not subject to twisting, bending, or displacement during flight. The reference IVHM system 326 provides a measure of structural change over a small period of time. In practice, the monitor 348 may measure real-time structural change such as twist relative to the reference IVHM systems but also may compute the twist between IVHM systems 324/328/330/332/334 at various measurement points.

These measurements may be used in various ways. In real-time, the measurements are generally used to control the airframe (wing) for performance. In ground or post processing, design data (e.g., comprising designed-to limits and the like) and the measurements are used to create a database for the airframe that then provides Vehicle Structural Health (VSH) thresholds for use in real-time decisions by the monitor 348. In real-time, the monitor 348 normally controls the structure for performance at cruise conditions, but also monitors the real-time twist data for Integrated Vehicle Health Management (IVHM) events. These events may be structural anomalies resulting from impact or aileron anomaly, or structural stress resulting from wind shear or gust conditions.

Upon detecting an IVHM event (non-optimal event), condition data are forwarded to the flight control subsystem (not shown) which prepares the IVHM controller module 340 to drive the airframe structure into a more favorable state such as, for example but without limitation, minimizing vibration or flutter due to structural excessive impact, compensating for aileron non-optimal operation, reducing airframe stress resulting from shear or gust, or other favorable state.

The non-optimal event may comprise, for example but without limitation, an in-flight operation, a stress from wind shear on a lift surface such as the fuselage 302, a stress from a debris impact on a lift surface such as the horizontal stabilizer 310, a stress from a gust on a lift surface such as the wing 304, a vibration or flutter on the wing 304, a fuselage flexure such as flexure on the fuselage 302, an excessive bending of the fuselage 302, a propulsion system anomaly such as an anomaly in the propulsion system 320 (engine 320), an excessive linear displacement, an excessive angular displacement, a structural fatigue, a control surface anomaly, a lift surface anomaly such as a winglet 346 anomaly, or other non-optimal event.

Figure 4:
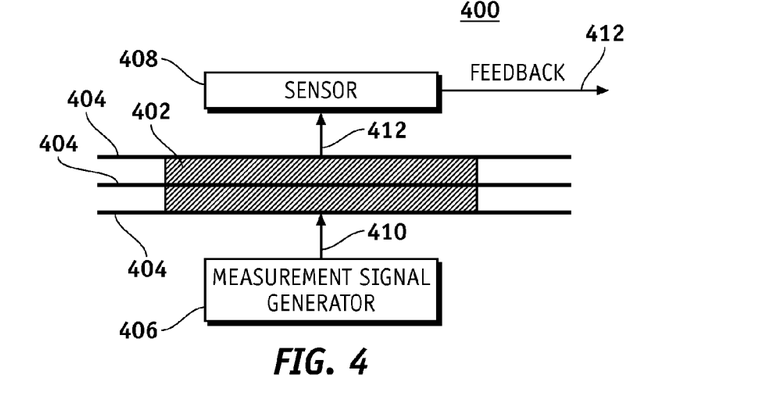
FIG. 4 is an illustration of an exemplary IVMH system according to an embodiment of the disclosure.

FIG. 4 is an illustration of an exemplary IVMH system 400 (IVHM systems 324/328/330/332/334 in FIG. 3) showing a plurality of anomaly detector structural members 404 (350 in FIG. 3) according to an embodiment of the disclosure. The IVHM system 400 may comprise a structure 402, the anomaly detector structural members 404, a measurement signal generator 406, and a sensor 408.

The structure 402 comprises for example, but without limitation, the control surfaces 306/308/314/316/318/344/354 and the lift surfaces 302/304/310 explained above. The structure 402 may be made from, for example but without limitation, composite material, or other material, and may be part of a vehicle such as the aircraft 300.

The anomaly detector structural members 404 are embedded in the structure 402 and may comprise, for example but without limitation, a carbon nanotube, a Bragg-grating embedded in an optical fiber (e.g., a fiber Bragg grating FBG), or other anomaly detector structural member embedded in the structure 402.

The measurement signal generator 406 is operable to generate a measurement signal 410. The measurement signal 410 is sent to the anomaly detector structural members 404 to determine whether a characteristic of the structure 402 has changed. The measurement signal 410 is received at the anomaly detector structural members 404. The anomaly detector structural members 404 each output a feedback signal 412 in response to receiving the measurement signal 410. A difference between the measurement signal 410 and the feedback signal 412 determines a change in the structure 402. The difference may be converted to structural parameters, such as but without limitation, twist, deflection, extension, displacement, or other structural design parameters to determine the change in the structure 402. In this manner, the change can be compared to an event threshold to allow ascertaining whether a load bearing structure such as the aircraft 300 is approaching a predesigned limit load as explained in more detail below. The measurement signal 410 may comprise a voltage signal, a light signal, or other signal.

The sensor 408 is operable to measure the feedback signal 412. The sensor 408 may comprise, for example but without limitation, a Bragg light measurement sensor, an Fe2O3 (iron oxide) bridge across a nanotube, a strain gauge, or other sensor that can be used for measuring the feedback signal 412. The feedback signal 412 from the anomaly detector structural members 404 as measured by the sensor 408 is feedback to the control system 336 (e.g., flight controls electronics) which controls dynamics of the aircraft 300. The feedback signal 412 may comprise a voltage feedback, a light feedback, a wavelength feedback, a brilliance feedback, or other signal feedback. For example, in one embodiment, each of the anomaly detector structural members 404 may comprise carbon nanotubes and the feedback signal 412 comprises a voltage feedback. For another example, in another embodiment, each of the anomaly detector structural members 404 comprises a Bragg-grating embedded in an optical fiber (e.g., a fiber Bragg grating FBG) and the feedback signal 412 comprises a wavelength feedback or a brilliance feedback. For a further example, in a further embodiment, the sensor 408 may comprise a strain gauge and the feedback signal 412 may comprise a voltage feedback indicating a strain (e.g., an amount of deformation due to an applied force) of the anomaly detector structural members 404.

In operation, the feedback signal 412 is sensed by the sensor 408. A structural health metrics calculator 710 (FIG. 7) calculates a difference between characteristics of the measurement signal 408 received at each of the anomaly detector structural members 404 and characteristics of the feedback signal 412 indicating a change in structural characteristics of the structure 402. The change may indicate a non-optimal event in the structure 402 when compared to an event threshold.

Characteristics of the measurements signal 410 and the feedback signal may comprise, for example but without limitation, a light intensity, a signal voltage, a signal amplitude, a signal phase, a signal wavelength, or other signal parameter.

Figure 5:
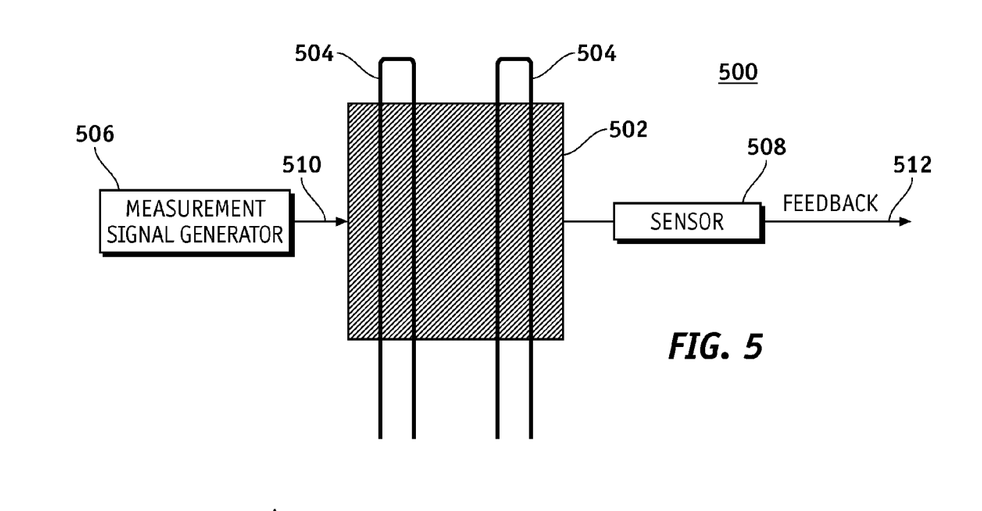
FIG. 5 is an illustration of an exemplary IVMH system according to an embodiment of the disclosure.

FIG. 5 is an illustration of an exemplary IVMH system 500 (IVHM systems 324/328/330/332/334 in FIG. 3) showing a plurality of anomaly detector structural members 504 (350 in FIG. 3) according to an embodiment of the disclosure. The IVHM system 500 may comprise a structure 502, the anomaly detector structural members 504, a measurement signal generator 506, and a sensor 508. The IVHM system 500 may have functions, material, and structures that are similar to the embodiments shown in IVHM system 400. Therefore common features, functions, and elements may not be redundantly described here.

Using an active feedback such as the feedback signal 412/512 from IVHM system 400-500 allows controlling the aircraft 300 closer to a limit of a structural design and getting a same performance while still meeting lifetime survivability goals.

Figure 6:
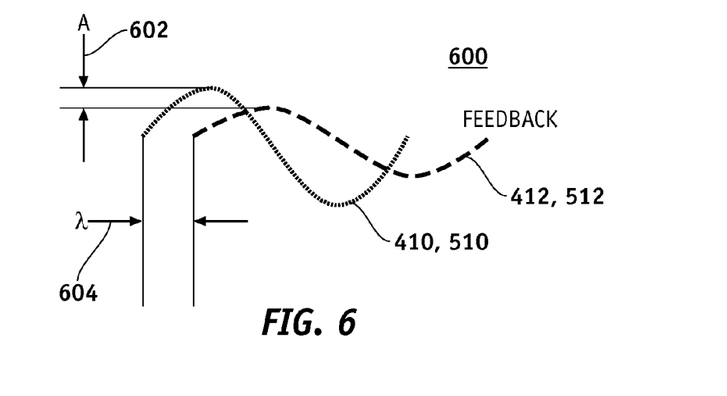
FIG. 6 is an illustration of an exemplary graph showing a measurement signal and a feedback signal of an exemplary IVMH system according to an embodiment of the disclosure.

FIG. 6 is an illustration of an exemplary graph 600 showing the measurement signal 410/510 and the feedback signal 412/512 of the IVMH system 400/500 in FIGS. 4-5 (IVHM systems 324/328/330/332/334 in FIG. 3) according to an embodiment of the disclosure. As mentioned above a difference between characteristics of the measurement signal 408 received at each of the anomaly detector structural members 404/504 and characteristics of the feedback signal 412/512 indicates a change in structural characteristics of the structure 402/502. For example, measurements signal 410/510 and the feedback signal 412/512 may be characterized by an amplitude and a phase and may differ in amplitude by A 602, or may differ in phase by A 604. The difference (e.g., the amplitude A 602 and the phase A 604) may be converted to the structural parameters mentioned above and may indicate a non-optimal event in the structure 402/502, if the difference exceeds an event threshold as explained in more detail below.

Figure 7:
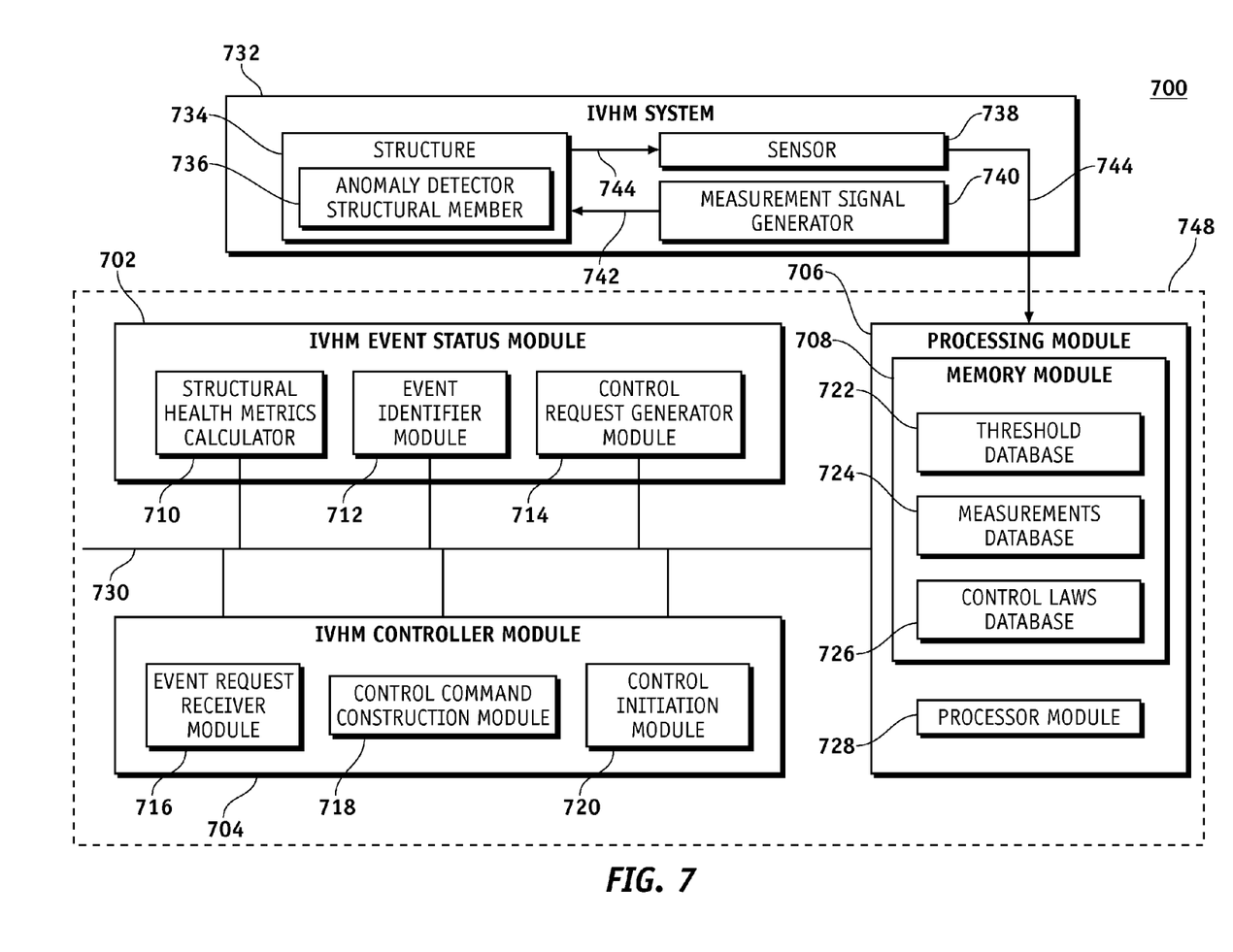
FIG. 7 is an illustration of an exemplary functional block diagram of a control system comprising an exemplary IVMH system according to an embodiment of the disclosure.

FIG. 7 is an illustration of an exemplary functional block diagram of a control system 700 (system 700) comprising an exemplary IVMH system 732 according to an embodiment of the disclosure. The system 700 controls and operate one or more control mechanisms in real-time to compensate for a non-optimal event that may be detected by the IVHM system 732. The system 700 may have functions, material, and structures that are similar to the embodiments shown in systems 324, 336, 400, 500 and 600. Therefore common features, functions, and elements may not be redundantly described here.

The various illustrative blocks, modules, processing logic, and circuits described in connection with system 700 may be implemented or performed with a general purpose processor, a content addressable memory, a digital signal processor, an application specific integrated circuit, a field programmable gate array, any suitable programmable logic device, discrete gate or transistor logic, discrete hardware components, or any combination thereof, designed to perform the functions described herein.

A processor may be realized as a microprocessor, a controller, a microcontroller, or a state machine. A processor may also be implemented as a combination of computing devices comprising hardware and/or software, e.g., a combination of a digital signal processor and a microprocessor, a plurality of microprocessors, one or more microprocessors in conjunction with a digital signal processor core, or any other such configuration.

The system 700 comprises the IVHM system 732 and the control system 748 (e.g., flight control electronics).

The IVMH system 732 may comprise a structure 734, an anomaly detector structural member 736, a sensor 738, and a measurement signal generator 740. A measurement signal 742 is generated by the measurement signal generator 740 and received by the anomaly detector structural member 736. The anomaly detector structural member 736 then outputs a feedback signal 744 in response to the measurement signal 742. The feedback signal 744 as measured by the sensor 738 is fed back to the control system 748 which controls dynamics of a vehicle such as the aircraft 300.

The control system 748 may comprise, for example but without limitation, a desktop, a laptop or notebook computer, a hand-held computing device (PDA, cell phone, palmtop, etc.), a mainframe, a server, a client, or any other type of special or general purpose computing device as may be desirable or appropriate for a given application or environment. The control system 748 generally comprises an IVHM event status module 702 (338 in FIG. 3), an IVHM controller module 704 (340 in FIG. 3), and a processing module 706 (342 in FIG. 3). The IVHM event status module 702 (338 in FIG. 3), the IVHM controller module 704 (340 in FIG. 3), and the processing module 706 (342 in FIG. 3) may be coupled to and communicate with each other via a network bus 730.

The IVHM event status module 702 may comprise the structural health metrics calculator 710, an event identifier module 712, and a control request generator module 714.

The structural health metrics calculator 710 is configured to calculate a difference between characteristics of the measurement signal 742 received at each anomaly detector structural member 736 and characteristics of the feedback signal 744 indicating a change in structural characteristics/parameters of the structure 734. The difference comprises signal characteristics such as, without limitation, voltage, light intensity, amplitude, and wavelength as explained above. The structural health metrics calculator 710 may convert the signal characteristics to corresponding structural parameters, such as but without limitation, twist, deflection, extension, displacement, or other structural design data that can be compared to an event threshold to allow ascertaining whether a load bearing structure such as the aircraft 300 is approaching a predesigned limit load as explained in more detail below.

The event identifier module 712 is configured to identify at least one non-optimal event in real-time if a change in the structure 734 exceeds an event threshold. The event threshold may comprise, for example but without limitation, nominal twist and twist gradients from tail to nose, wing tip to wing tip, reference IVHM system 326 to each IVHM system 324/328-334, landing gear jerk and acceleration, or other measurement. These may be compiled in real-time during flight and later offloaded for ground processing into a flight database such as a measurements database 724 (e.g., initially seeded with vehicle design data). The measurements database 724 may be used to extract the event threshold using stochastic estimation or other predictive algorithms.

For example, design data and real-time data collected over a number of flights may be used to create a flight database for an example vehicle in ground post-processing. The measurements database 724 may comprise data, for example but without limitation, a highly flexible vehicle structure comprising, for example but without limitation, a twist from end to end of about 7 degrees with about 95% confidence. From this information, a not to exceed gradient threshold (event threshold) may be established along with rules for engagement of an active control event.

For example, if the structure 734 twists to exceed about 7 degrees with a twist gradient greater than about 1 degree/sec (event threshold), the event identifier module 712 indicates a non-optimal event. An active control may then be initiated by the control initiation module 720 to alleviate structural stress by using a control mechanism to null out the gradient and return the structure 734 to a twist of about 7 degrees. The control mechanism may comprise, for example but without limitation, a propulsion system, controllable lift surfaces, flight control surfaces, active flow control, shaped metal alloys or other active structural materials that expand or contract as a function of a control signal, or other mechanism.

Additionally, if the gradient is less than about 1 deg/sec but the twist exceeds about 9 degrees with about 95% confidence, the event identifier module 712 identifies a non-optimal event, and active control is initiated by the control initiation module 720 to reduce this twist back to about 7 degrees. As an example, the monitor 348 (FIG. 3) measures in real-time a twist of about 7 degrees with a gradient of about 1 deg/sec and when it passes through 7 degrees twist with this gradient, the twist and gradient indicate the structure 734 may continue to stress further out of tolerance. In response, a control event is initiated by the control initiation module 720 to null out the twist gradient and drive the twist back towards 7 degrees. In an alternate example, the real-time twist may reach about 9 degrees with about 95% confidence with little to no twist gradient. In response, an active control event is initiated by the control initiation module 720 to reduce structural stress back towards 7 degrees.

The control request generator module 714 is configured to generate a control request signal and send the control request signal to the IVHM controller module 704.

The IVHM controller module 704 may comprise an event request receiver module 716, a control command construction module 718, and a control initiation module 720. The IVHM controller module 704 may be a standalone flight control system or a subsystem of the flight control system of the aircraft 300.

The event request receiver module 716 is configured to receive an active control request from the control request generator module 714.

The control command construction module 718 is configured to construct an active control command based on the control request signal.

The control initiation module 720 activates a control mechanism in response to an active control command in real-time to compensate for the non-optimal event as explained above. The activating of the control mechanism may comprise mechanism activation of, for example but without limitation, a control surface actuation, a lift surface actuation, a propulsive power alteration, active flow control, flow control actuation, actuation of shaped memory alloys or other active structural materials that expand or contract as a function of a control signal, a combination thereof, or other control mechanism.

The lift surfaces 302/304/310, or other lift surfaces provide lift as a function of engine thrust, while the control surfaces 306/308/314/316/318/344/354 or other control surfaces may be moved by means of actuators 352 (FIG. 3) to control the aircraft flight path, commonly called flight control. Additionally, the actuators 352 may comprise skin/structure actuators or other actuators that may be used for flexing the lift surfaces 302/304/310, to a more desirable (e.g., fuel efficient) shape based on measured flight conditions received from the processing module 706.

For example but without limitation, the control initiation module 720 may be operable to control a position of the flap 344, control a position of the slat 306, control a position of the spoiler 354 via control of actuators 352 (FIG. 3), or other control function.

The control initiation module 720 receives data from a control laws database 726 of the processing module 706 that provides a desired position of the control surfaces 306/308/314/316/318/344/354 and lift surfaces 302/304/310 suitable to alleviate a structural anomaly such as a flexure, displacement or twist of a structure of the aircraft 300.

For example, if the aircraft 300 receives a gust on one side, the control initiation module 720 reacts quickly to keep stress from becoming too great to deform the wing 304. For another example, if turbulence leads to vibration or flutter, and causes the structure 734 of the aircraft 300 to enter a resonant frequency, a motion is sensed through measurements. After the motion is sensed, the active control command construction module 718 of the IVHM controller module 704 generates a command for the control initiation module 720 to null out the vibration or flutter. In another example, the system 700 can also alleviate stress on at least one part of a fuselage such as an upper mid-body flexing of the fuselage 302.

In this manner, the system 700 actively controls the aircraft 300 in real-time in response to an event in various flight conditions such as takeoff, cruise, approach and landing, and the like, without an operator/pilot interaction. However, in one embodiment, an operator/pilot can suitably override/prevent action commanded by the control initiation module 720 during the various flight conditions.

In the embodiment shown in FIG. 3, a commercial airplane is shown. It will be readily apparent to those of ordinary skill in the art, that the embodiment shown in FIG. 3 can have application or be adapted to non-traditional structures such as, but without limitation, high altitude long endurance vehicles whose entire structure may be a controllable highly flexible lift surface, and the like.

The illustrated embodiment is but one example, and those skilled in the art will appreciate that multiple leading and trailing edge configurations can be used, and that multiple configurations of the corresponding actuators will therefore can be used, as well as the lift surface actuators mechanically coupled to the wing structure itself (e.g., rather than a flight control surface), or any control or lift surface of the aircraft (e.g., and not just those on the wing). Moreover, as mentioned above, the embodiments are not limited to aircraft structure and may also be applicable to, for example but without limitation, any manned and unmanned ground, air, space, water and underwater vehicles, buildings, windmills, and the like.

The processing module 706 may comprise a memory module 708, and processor module 728.

The processor module 728 comprises processing logic that is configured to carry out the functions, techniques, and processing tasks associated with the operation of the system 700. In particular, the processing logic is configured to support the system 700 described herein. For example, processor module 728 may provide data from the memory module 708 to the IVHM controller module 704. For another example, the processor module 728, in one embodiment, provides desired positional changes from the control laws database 726 to the control initiation module 720, which in turn uses the raw data to calculate adjustments to be made to control surfaces 306/308/314/316/318/344/354 and the lift surfaces 302/304/310, via operation of one or more of the various actuators described above.

In this manner, the processor module 728 also accesses data stored in a database, such as databases 722, 724 and 726, to support functions of the system 700. Thereby, the processor module 728 enables active control of the aircraft 300. The data may comprise, for example but without limitation, airspeed, altitude, event threshold, desired position of a control surface (e.g., aileron 308) and desired position of a lift surface (e.g., wing 304), a measurement signal, a feedback signal, structural characteristics, parameters, or other data, as explained in more detail below.

The processor module 728 may be implemented, or realized, with a general purpose processor, a content addressable memory, a digital signal processor, an application specific integrated circuit, a field programmable gate array, any suitable programmable logic device, discrete gate or transistor logic, discrete hardware components, or any combination thereof, designed to perform the functions described herein. In this manner, a processor may be realized as a microprocessor, a controller, a microcontroller, a state machine, or the like. A processor may also be implemented as a combination of computing devices comprising hardware and/or software, e.g., a combination of a digital signal processor and a microprocessor, a plurality of microprocessors, one or more microprocessors in conjunction with a digital signal processor core, or any other such configuration.

The memory module 708 may be a data storage area with memory formatted to support the operation of the system 700. The memory module 708 is configured to store, maintain, and provide data as needed to support the functionality of the system 700 in the manner described below. In some embodiments, the memory module 708 may comprise, for example but without limitation, a non-volatile storage device (e.g., non-volatile semiconductor memory, hard disk device, optical disk device, and the like), a random access storage device (e.g., SRAM, DRAM), or any other form of storage medium known in the art.

The memory module 708 may be coupled to the processor module 728 and configured to store, for example but without limitation, a VSH threshold database 722, the measurements database 724, a control laws database 726, or other database. Additionally, the memory module 708 may represent a dynamically updating database containing a table for updating the databases 722-726, or other application. The memory module 708 may also store, a computer program that is executed by the processor module 728, an operating system, an application program, tentative data used in executing a program, or other data and application.

The memory module 708 may be coupled to the processor module 728 such that the processor module 728 can read information from and write information to the memory module 708. As an example, the processor module 728 and memory module 708 may reside in respective application specific integrated circuits (ASICs). The memory module 708 may also be integrated into the processor module 728. In an embodiment, the memory module 708 may comprise a cache memory for storing temporary variables or other intermediate information during execution of instructions to be executed by the processor module 728.

The VSH threshold database 722 comprises, for example but without limitation, the VSH threshold derived from aeroelasticity measurements, or other data. The VSH threshold may be used to determine the event threshold as explained above. Data from the measurements database 724 may be used to construct or update one or more VSH thresholds stored in the VSH threshold database 722, thereby updating the VSH threshold database 722.

The measurements database 724 comprises measurements such as measurements of, for example but without limitation, twist, body bending, displacement, jerk, attitudes, rates, or other measurement. The measurements database 724 may also comprises parameters associated with these measurements such as, but without limitation, altitude, type (e.g., airplane type), model, weight, or other parameter.

The control law database 726 comprises desired control surface positions, desired lift surface positions based on current flight conditions (e.g., speed, altitude, Mach).

Figure 8:
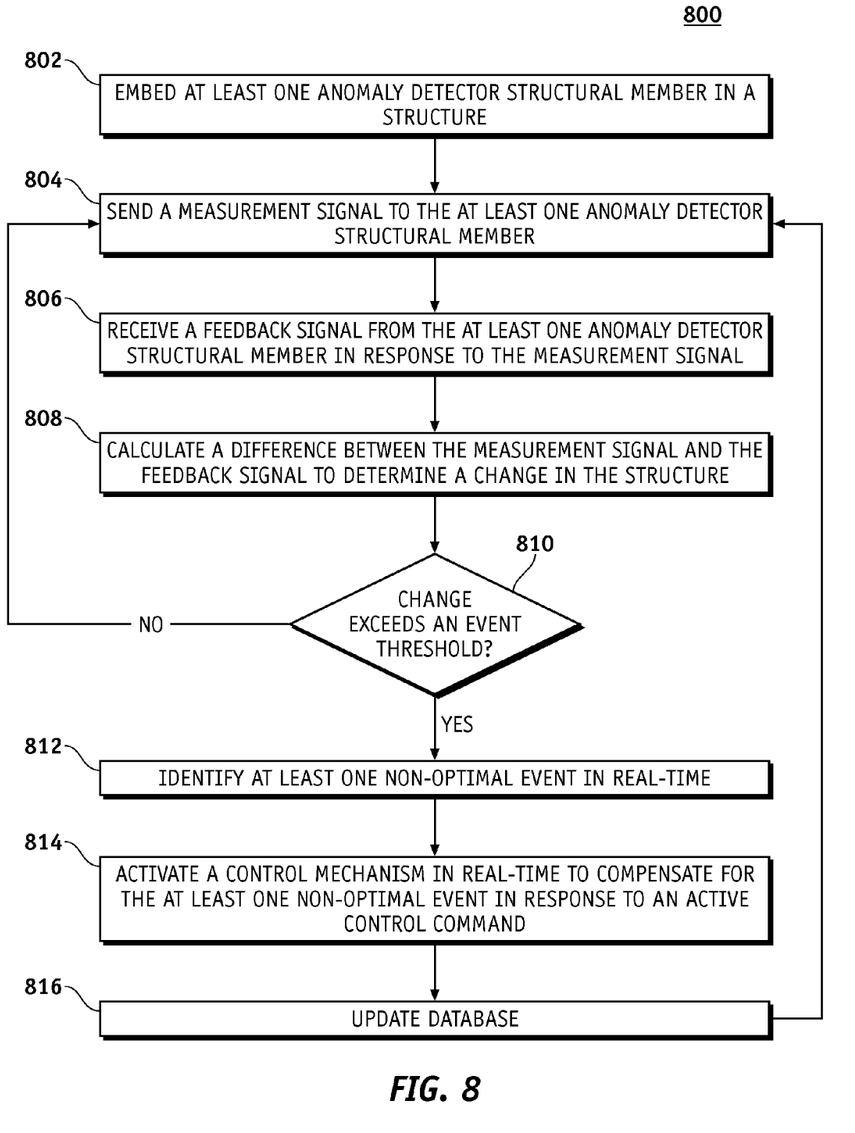
FIG. 8 is an illustration of an exemplary flowchart showing a process for alleviating an anomaly in a structure according to an embodiment of the disclosure.

FIG. 8 is an illustration of an exemplary flowchart showing a process 800 for alleviating an anomaly in a structure according to an embodiment of the disclosure. The various tasks performed in connection with process 800 may be performed mechanically, by software, hardware, firmware, a computer-readable medium having computer executable instructions for performing the process method, or any combination thereof. It should be appreciated that process 800 may include any number of additional or alternative tasks, the tasks shown in FIG. 8 need not be performed in the illustrated order, and process 800 may be incorporated into a more comprehensive procedure or process having additional functionality not described in detail herein.

For illustrative purposes, the following description of process 800 may refer to elements mentioned above in connection with FIGS. 3-7. In practical embodiments, portions of the process 800 may be performed by different elements of the system 700 such as: IVHM system 732, the IVHM event status module 702, the IVHM controller module 704, the processing module 706, and the network bus 730. Process 800 may have functions, material, and structures that are similar to the embodiments shown in FIGS. 3-7. Therefore common features, functions, and elements may not be redundantly described here.

Process 800 may begin by embedding at least one anomaly detector structural member such as the anomaly detector structural member 736 in a structure such as the structure 734 (task 802).

Process 800 may continue by sending a measurement signal such as the measurement signal 742 to the anomaly detector structural member 736 (task 804).

Process 800 may continue by receiving a feedback signal such as the feedback signal 744 from the anomaly detector structural member 736 in response to the measurement signal 742 (task 806).

Process 800 may continue by calculating a difference between the measurement signal 742 and the feedback signal 744 to determine a change in the structure 734 (task 808).

Process 800 may continue by determining whether the change exceeds an event threshold (inquiry task 810). The event threshold allows ascertaining whether a load bearing structure such as the structure 402/502/734 is approaching a predesigned limit load. As explained above in one example, the event threshold may be based on a twist from end to end of about 7 degrees with about 95% confidence. The event threshold may be set to structure twists exceeding 7 degrees with a twist gradient greater than 1 degree/sec.

If the change in the measurement signal exceeds the event threshold (YES branch of inquiry task 810), structural health metrics warrant additional control, and the event identifier module 712 may continue by identifying at least one non-optimal event in real-time (task 812). Thus, for this example, the event identifier module 712 indicates a non-optimal event in response to the structure twist exceeding 7 degrees with the twist gradient greater than 1 degree/sec.

Process 800 may continue by activating a control mechanism in real-time to compensate for the at least one non-optimal event (task 814). Alternatively, the process 800 may notify a pilot/operator of the non-optimal event so that they can make an appropriate correction, alleviating the non-optimal event, or land at nearest suitable airport if the change exceeds the event threshold. Task 814 then goes back to task 804.

In this manner, a non-optimal structural event is alleviated in real-time using a feedback signal from an anomaly detector structure member embedded in a structure. Alleviating the non-optimal structural event prolongs the structural life of the structure such as the aircraft 300.

If the change does not exceed the event threshold (NO branch of inquiry task 808), then structural health metrics do not warrant additional control, and process 800 goes to task 804.

Process 800 may continue by a processing module such as the processing module 706 updating measurement database such as the measurements database 724 and a threshold database such as the VSH threshold database 722 (task 816) to obtain updated event thresholds. The processing module 706 updates a flight aeroelasticity record that comprises elasticity measurements, gradients, current event thresholds and other relevant data such as aircraft load data, cruise condition, or other data. The flight aeroelasticity record is provided to the monitor 348 and is processed in a post-flight VSH to form a reference database such as the measurements database 724 for the vehicle (e.g., aircraft 300) from which the VSH thresholds and rules for engaging a structural health management event are derived.

During flight, the system 700 updates the VSH threshold database 722 and the measurements database 724 in real-time in the task 816 for post-flight processing. The measurements database 724 comprises current data. However, in some embodiments, the measurements database 724 and the VSH threshold database 722 may be updated in the task 814 in real-time in response to a non-optimal condition such as a control surface or propulsion anomaly. A series of major and minor repairs on a structure of the aircraft 300 can be scheduled by analyzing trends in a structure fatigue as recorded in the VSH threshold database 722 and the measurements database 724 and a probability of an unanticipated non-optimal structural condition can be reduced. In this manner a new (updated) set of variables including structural health metrics is created and can be used to control the aircraft 300.

A plurality of updated strain measurements is sent to the system 700, and actuation of the actuators and surfaces are updated to alleviate a structural anomaly of load bearing structures while maintaining a configuration of the load bearing structures for continued flight on a real time basis. Maneuvering the actuators and surfaces and follow-on updating of the actuation of the actuators and surfaces optimizes performance metrics of the vehicle, shaping the strain profile of the load bearing structure to a desired design.

Historical records of an accumulated fatigue anomaly of the load bearing structure are updated at a designed rate which is a count of an accumulated fatigue anomaly in the load bearing structures due to the updates of the actuation of the actuators and surfaces.

Figure 9:
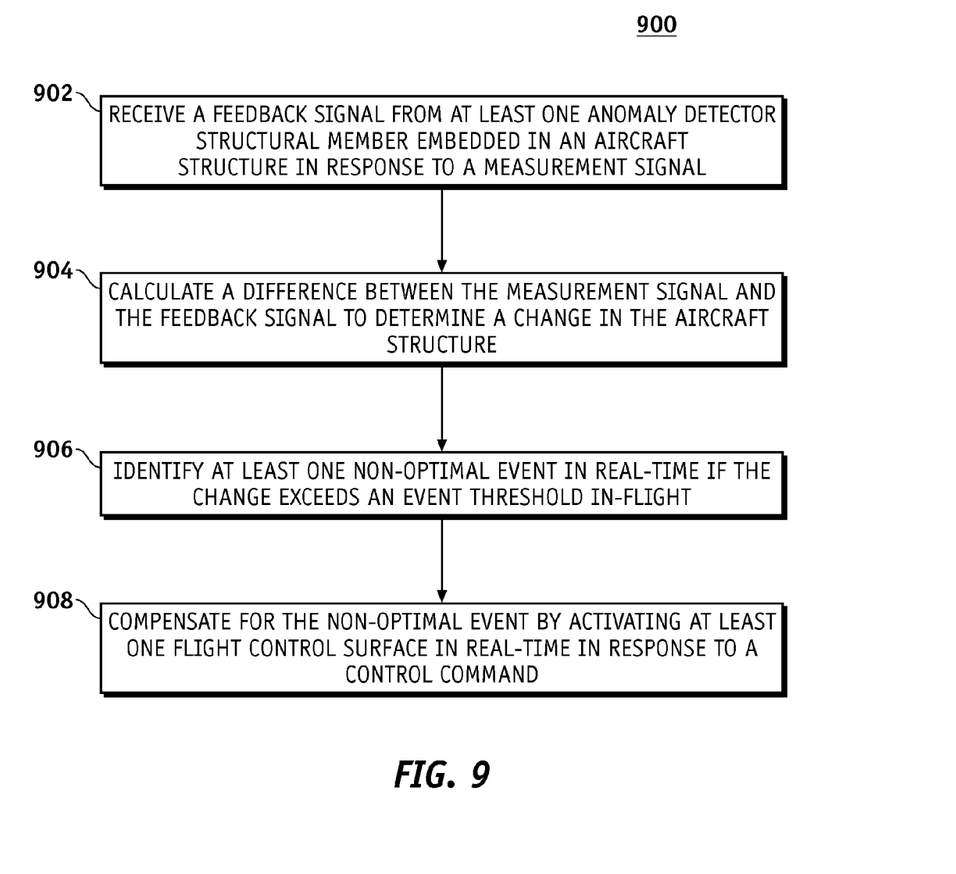
FIG. 9 is an illustration of an exemplary flowchart showing a flight control process for actively compensating for a non-optimal event in an aircraft structure in-flight according to an embodiment of the disclosure.

FIG. 9 is an illustration of an exemplary flowchart showing a flight control process 900 for actively compensating for a non-optimal event in an aircraft structure in-flight according to an embodiment of the disclosure. The various tasks performed in connection with process 900 may be performed mechanically, by software, hardware, firmware, a computer-readable medium having computer executable instructions for performing the process method, or any combination thereof. It should be appreciated that process 900 may include any number of additional or alternative tasks, the tasks shown in FIG. 9 need not be performed in the illustrated order, and process 900 may be incorporated into a more comprehensive procedure or process having additional functionality not described in detail herein.

For illustrative purposes, the following description of process 900 may refer to elements mentioned above in connection with FIGS. 3-7. In practical embodiments, portions of the process 900 may be performed by different elements of the system 700 such as: The IVMH system 732, the IVHM event status module 702, the IVHM controller module 704, the processing module 706, and the network bus 730. Process 900 may have functions, material, and structures that are similar to the embodiments shown in FIGS. 3-8. Therefore common features, functions, and elements may not be redundantly described here.

Process 900 may begin by receiving a feedback signal such as the feedback signal 744 from at least one anomaly detector structural member such as the anomaly detector structural member 736 embedded in an aircraft structure such as the structure 734 in response to a measurement signal such as the measurement signal 742 (task 902).

Process 900 may continue by calculating a difference between the measurement signal 742 and the feedback signal 744 to determine a change in the aircraft structure (task 904).

Process 900 may continue by identifying at least one non-optimal event in real-time if the change exceeds an event threshold in-flight (task 906).

Process 900 may continue by compensating for the non-optimal event by activating at least one flight control surface in real-time in response to a control command (inquiry task 908).

The above description refers to elements or nodes or features being "connected" or "coupled" together. As used herein, unless expressly stated otherwise, "connected" means that one element/node/feature is directly joined to (or directly communicates with) another element/node/feature, and not necessarily mechanically. Likewise, unless expressly stated otherwise, "coupled" means that one element/node/feature is directly or indirectly joined to (or directly or indirectly communicates with) another element/node/feature, and not necessarily mechanically. Thus, although FIGS. 3-7 depict example arrangements of elements, additional intervening elements, devices, features, or components may be present in an embodiment of the disclosure.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; and adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future.

Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent. The term "about" when referring to a numerical value or range is intended to encompass values resulting from experimental error that can occur when taking measurements.

The invention claimed is:

1. A method for alleviating an anomaly in a structure, the method comprising:
   embedding at least one anomaly detector structural member in the structure;
   sending a measurement signal to the at least one anomaly detector structural member;
   receiving a feedback signal from the at least one anomaly detector structural member in response to the measurement signal;
   calculating in real-time a difference between the measurement signal and the feedback signal to determine a real-time change in the structure;
   identifying at least one non-optimal event in real-time if the real-time change exceeds an event threshold; and
   altering in real-time dynamics control laws of a controller of the structure to control according to a new set of variables based on the real-time change in the structure to provide updated dynamics control laws.

2. The method of claim 1, further comprising activating a control mechanism in real-time based on the updated control laws to alleviate a structural anomaly in the structure due to the at least one non-optimal event in response to an active control command.

3. The method of claim 2, wherein the at least one anomaly detector structural member comprises a plurality of anomaly detector structural members that are linearly configured along the structure and comprises at least one member selected from the group consisting of: a Bragg-grating embedded in an optical fiber, and a carbon nanotube.

4. The method of claim 2, wherein the structure comprises an aircraft.

5. The method of claim 4, wherein the at least one non-optimal event comprises an in-flight operation.

6. The method of claim 1, wherein the event threshold comprises a Vehicle Structural Health (VSH) threshold determined by a predictive algorithm based on the measurement signal.

7. The method of claim 1, wherein the step of identifying of the at least one non-optimal event comprises identifying at least one member selected from the group consisting of: a wind shear, a vibration, a flutter, a flexure, a linear displacement, an angular displacement, and a structural fatigue.

8. A system for alleviating an anomaly in a structure in real-time, the system comprising:
   a structure;
   at least one anomaly detector structural member embedded in the structure;
   a measurement signal generator operable to send a measurement signal to the at least one anomaly detector structural member;
   a sensor operable to receive a feedback signal from the at least one anomaly detector structural member in response to the measurement signal;
   a structural health metrics calculator operable to calculate in real-time a difference between the measurement signal and the feedback signal to determine a real-time change in the measurement signal;
   an event identifier module operable to identify at least one non-optimal event in real-time if the real-time change exceeds an event threshold;
   a controller operable to alter in real-time dynamics control laws to control according to a new set of variables based on the real-time change in the structure to provide updated dynamics control laws; and
   a control initiation module operable to activate a control mechanism based on the updated dynamics control laws in response to an active control command in real-time to alleviate a structural anomaly in the structure due to the at least one non-optimal event.

9. The system of claim 8, wherein the at least one anomaly detector structural member comprises a plurality of anomaly detector structural members that are linearly configured along the structure and comprises at least one member selected from the group consisting of: a Bragg-grating embedded in an optical fiber, and a carbon nanotube.

10. The system of claim 8, wherein the sensor comprises at least one member selected from the group consisting of: a Bragg light measurement sensor, an $Fe_2O_3$ bridge across a carbon nanotube, and a strain gauge.

11. The system of claim 8, wherein the structure comprises an aircraft.

12. The system of claim 11, wherein activating the control mechanism comprises at least one member selected from the group consisting of: a control surface actuation, a lift surface actuation, a flow control actuation, actuation of shaped memory alloys, actuation via active structural materials, and a propulsive power alteration.

13. The system of claim 11, wherein the non-optimal event comprises at least one member selected from the group consisting of: structural stress from wind shear, structural stress from gust, vibration, flutter, flexure, linear displacement, angular displacement, and structural fatigue.

14. The system of claim 8, further comprising a measurements database, a threshold database, and a control laws database.

15. The system of claim 14, further comprising a processing module operable to update the measurements database and the threshold database in real-time.

16. A flight control method for actively preventing a non-optimal event in an aircraft structure in-flight, the method comprising:
   receiving a feedback signal from at least one anomaly detector structural member embedded in the aircraft structure in response to a measurement signal;
   calculating in real-time a difference between the measurement signal and the feedback signal to determine a real-time change in the aircraft structure;
   identifying at least one non-optimal event in real-time if the change exceeds an event threshold in-flight;
   altering in real-time dynamics control laws of a controller of the aircraft structure to control according to a new set of variables based on the change in the structure to provide updated dynamics control laws; and
   alleviating a structural anomaly due to the at least one non-optimal event based on the updated dynamics control laws by activating at least one flight control surface in real-time in response to a control command.

17. The method of claim 16, wherein the identifying of the at least one non-optimal event comprises identifying of at least one member selected from the group consisting of: a stress from wind shear on a lift surface, a stress from a debris impact on a lift surface, a stress from a gust on a lift surface, a vibration, a flutter, a fuselage flexure, an excessive bending of the fuselage, a propulsion system anomaly, an excessive linear displacement, an excessive angular displacement, a structural fatigue, a control surface anomaly, and a lift surface anomaly.

18. The method of claim 16, wherein the at least one anomaly detector structural member comprises a plurality of anomaly detector structural members that are linearly configured along the structure and comprises at least one member selected from the group consisting of: a Bragg-grating embedded in an optical fiber, and a carbon nanotube.

19. The method of claim 16, wherein the feedback signal is sensed by at least one sensor selected from the group consisting of: a Bragg light measurement sensor, an $Fe_2O_3$ bridge across a carbon nanotube, and a strain gauge.

20. The method of claim 2, wherein activating the control mechanism comprises: a flow control actuation, or actuation of a shaped memory alloy.

\* \* \* \* \*